(12) United States Patent
Miyazaki et al.

(10) Patent No.: US 6,437,862 B1
(45) Date of Patent: Aug. 20, 2002

(54) DEFECT INSPECTION APPARATUS

(75) Inventors: Yoko Miyazaki; Masahiko Ikeno, both of Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/457,334

(22) Filed: Dec. 9, 1999

(30) Foreign Application Priority Data

Jun. 22, 1999 (JP) .......................................... 11-174951

(51) Int. Cl.⁷ .............................................. G01N 21/00
(52) U.S. Cl. ................. 356/237.2; 356/237.5; 250/559.4; 250/205
(58) Field of Search ......................... 356/237.1, 237.2, 356/237.3, 237.4, 237.5, 237.6, 237.7, 394; 250/559.01, 559.06, 559.41, 559.4, 559.45, 205

(56) References Cited

U.S. PATENT DOCUMENTS

| 3,972,624 | A | * | 8/1976 | Klein et al. | |
| 4,918,321 | A | * | 4/1990 | Klenk et al. | ................. 356/445 |
| 5,305,079 | A | * | 4/1994 | Albrecht et al. | ............ 356/237 |
| 5,617,203 | A | * | 4/1997 | Kobayashi et al. | ......... 356/237 |
| 5,774,222 | A | * | 6/1998 | Maeda et al. | ................ 356/394 |
| 6,016,562 | A | | 1/2000 | Miyazaki et al. | ........... 714/724 |
| 6,031,607 | A | * | 2/2000 | Miyazaki | ................. 356/237.1 |

FOREIGN PATENT DOCUMENTS

| JP | 2635758 | | 4/1997 |
| JP | 10-22209 | * | 1/1998 |
| JP | 2822937 | | 9/1998 |

* cited by examiner

*Primary Examiner*—Hoa Q. Pham
(74) *Attorney, Agent, or Firm*—Oblon, Spivak, McClelland, Maier & Neustadt, P.C.

(57) ABSTRACT

A defect inspection apparatus includes a first main controller for producing a reflectance distribution in a wafer surface to generate illumination light control data, based on the reflectance distribution, the illumination light control data being control data for adjusting the intensity of illumination light so that the intensity of reflected light from all locations in the wafer surface reaches an average intensity value, and a filter controller for inputting a filter control signal to a filter, based on the illumination light control data. The transmittance or reflectance of the filter for illumination light is controlled by the filter control signal. Consequently, the intensity of light reflected from a wafer to be inspected is controlled to provide uniformity in the wafer surface. Therefore, the defect inspection apparatus detects a defect occurring in the object to be inspected with high accuracy.

11 Claims, 13 Drawing Sheets

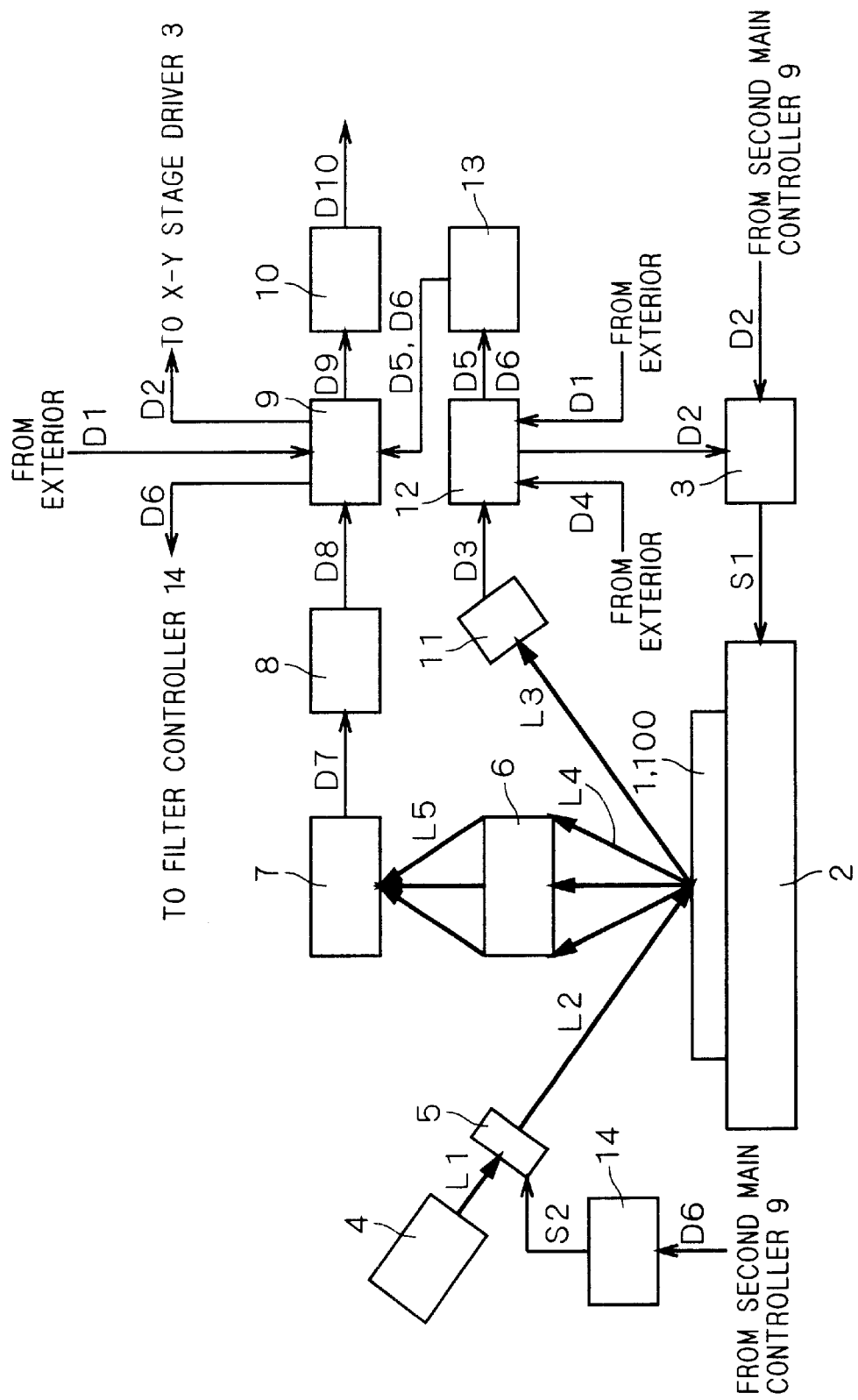
F I G. 1

F I G . 1 1
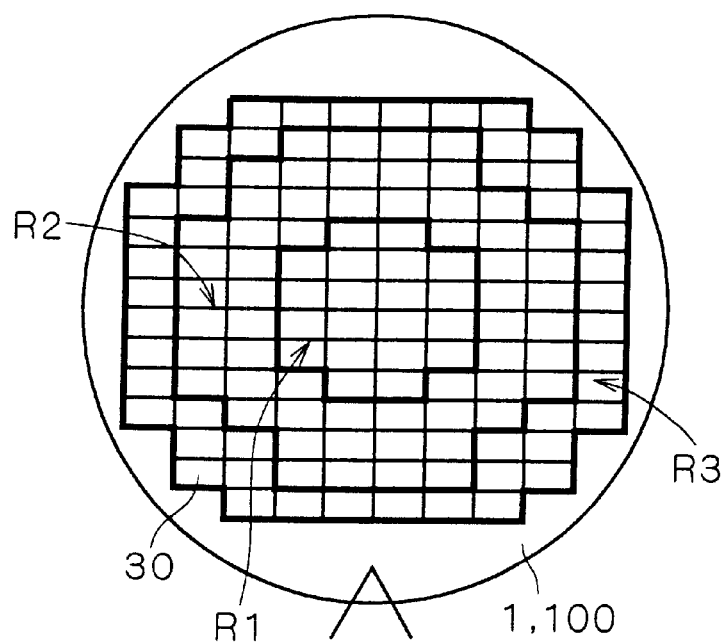
F I G . 1 2
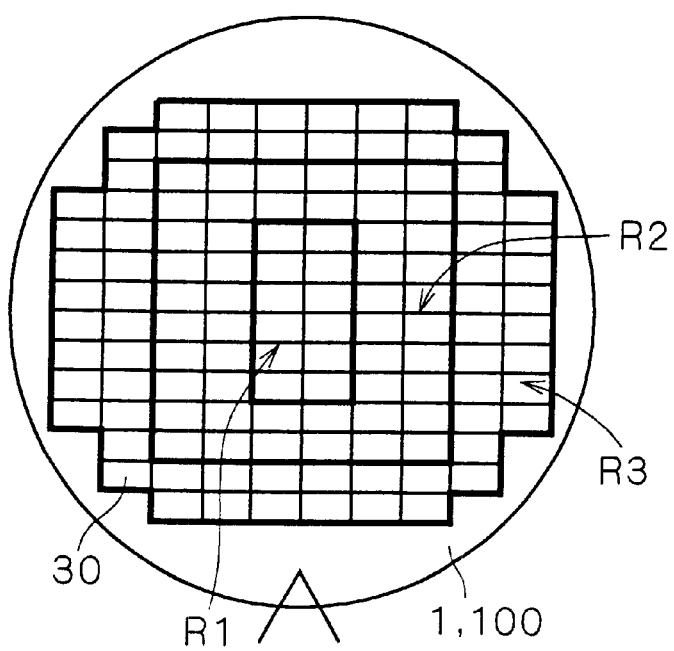

DEFECT INSPECTION APPARATUS

BACKGROUND OF THE INVENTION

1. Field of the Invention

The present invention relates to a defect inspection apparatus for inspecting an object, such as a wafer and a chip, for defects.

2. Description of the Background Art

Defects include extraneous material adhering to a surface of an object, and a pattern defect of an object. A semiconductor device will be taken as an example of the objects to be inspected in the description below.

FIG. 19 is a schematic block diagram of a background art defect inspection apparatus. As illustrated in FIG. 19, the background art defect inspection apparatus comprises an X-Y stage 101 for placing thereon a wafer 100 to be inspected, an objective lens 102, a Xe lamp 103, a TV camera 104, an A/D converter 105, an image memory 106, and a defect judgement device 107. FIG. 20 is a partially enlarged top plan view of the wafer 100. As illustrated in FIG. 20, the wafer 100 has a plurality of chips 110 arranged in a matrix.

Description is given on a method of inspecting a circuit pattern 111b fabricated into a chip 110b for defects, using the defect inspection apparatus shown in FIG. 19. First, the X-Y stage 101 is moved to position the wafer 100 so that the Xe lamp 103 illuminates the circuit pattern 111b. Next, the Xe lamp 103 directs light onto the circuit pattern 111b. The light reflected from the circuit pattern 111b passes through the objective lens 102 and reaches the TV camera 104. The TV camera 104 detects the reflected light as an image. The A/D converter 105 converts the detected image into a digital signal to input the digital signal as image data DB to the defect judgement device 107.

The image memory 106 has previously inputted image data DA concerning a circuit pattern 111a fabricated into a chip 110a. The defect judgement device 107 receives the image data DA from the image memory 106, and then subtracts the image data DA from the image data DB to determine a difference therebetween. FIG. 21 shows the image data DA, the image data DB, and the difference data DB–DA. The image data DA, DB and the difference data DB–DA are shown in plan view in the upper part of FIG. 21, and a digital value representing brightness as measured along the line L is illustrated in the lower part of FIG. 21. If the circuit pattern 111b has a defect, the defect appears as defect data 112 in the image data DB. When the brightness of the defect data 112 is not less than a predetermined threshold value X1 as a result of the subtraction of the image data DA from the image data DB, the defect judgement device 107 judges that the circuit pattern 111b has a defect in a position corresponding to the defect data 112.

However, such a background art defect inspection apparatus has presented problems to be described below.

First Problem

As described hereinabove, the background art defect inspection apparatus compares the value of the difference data DB–DA provided by subtracting the image data DA from the image data DB with the predetermined threshold value X1 to judge the presence or absence of a defect. A wafer subjected to the CMP process often has different thicknesses depending on locations in the wafer surface. In such a case, the difference in thickness causes a difference in reflected light intensity. Thus, the value of the difference data DB–DA is not zero but is detected as noises in a nondefective location (FIG. 22). It is therefore difficult to determine whether the difference data DB–DA having a value not less than the threshold value X1 results from a defect or noises. The use of a higher threshold value X2 so as not to detect noises makes it impossible to detect the defect data. Additionally, in combination with the decrease in pattern resolution when detected due to performance limitations of optical systems with recent size reduction of semiconductor devices, the background art defect inspection apparatus presents the problem of low defect detection accuracy.

Second Problem

Some defects in a chip are fatal to semiconductor devices, but some are not. This depends on the positions in which the defects occur in a chip. However, the background art defect inspection apparatus detects all defects in the chip independently of the positions in which the defects occur. Hence, the background art defect inspection apparatus is not capable of judging whether or not the detected defects affect a yield in practice. This results in delayed measures against process failures and the production of dust which give rise to defects, accordingly leading to the increase in manufacturing costs.

SUMMARY OF THE INVENTION

According to a first aspect of the present invention, a defect inspection apparatus comprises: a light illuminator for directing light onto a surface of an object to be inspected; a data generator for generating illumination light control data for rendering the intensity of light reflected from the surface uniform throughout the surface, based on a distribution of reflectance of the surface for the light; a light intensity controller for controlling the intensity of the light directed from the light illuminator onto the surface, based on the illumination light control data; and an inspector receiving the light reflected from the surface or scattered by the surface and for inspecting the surface for a defect.

Preferably, according to a second aspect of the present invention, in the defect inspection apparatus of the first aspect, the light intensity controller includes: a liquid crystal filter having a filter surface disposed in an optical path between the light illuminator and the surface; and a filter controller for controlling transmittance of the filter surface for the light, based on the illumination light control data.

Preferably, according to a third aspect of the present invention, in the defect inspection apparatus of the second aspect, the liquid crystal filter is a filter capable of non-uniformly controlling the transmittance in the filter surface.

Preferably, according to a fourth aspect of the present invention, in the defect inspection apparatus of any one of the first to third aspects, the object is a wafer having a surface coated with a film.

Preferably, according to a fifth aspect of the present invention, in the defect inspection apparatus of any one of the first to third aspects, the object is a wafer having a plurality of chips arranged in a matrix; the data generator generates the illumination light control data based on the reflectance for each of the chips or for each of dice; and the light intensity controller controls the intensity of the light for each of the chips or for each of the dice.

Preferably, according to a sixth aspect of the present invention, in the defect inspection apparatus of any one of the first to third aspects, the object is a wafer having a plurality of chips arranged in a matrix; the data generator receives classification data concerning the plurality of chips classified into a first group of chips and a second group of chips in accordance with a predicted distribution of the reflectance of a wafer surface of the wafer; the data generator determines a first reflectance of at least one representative first chip included in the first group as the reflectance of the first group of chips, and determines a second reflectance of at least one representative second chip included in the second group as the reflectance of the second group of chips; and the light intensity controller controls the intensity of the light for each of the first and second groups.

Preferably, according to a seventh aspect of the present invention, in the defect inspection apparatus of any one of the first to third aspects, the object is a wafer having a plurality of chips arranged in a matrix; the data generator receives classification data concerning the plurality of chips classified into a first group of chips expected to be more susceptible to defects and a second group of chips expected to be less susceptible to defects; the data generator determines the reflectance for each of the first group of chips or for each of the dice of the first group of chips, and determines the reflectance of at least one representative chip included in the second group as the reflectance of the second group of chips; and the light intensity controller controls the intensity of the light for each of the first group of chips or for each of the dice of the first group of chips, and controls the intensity of the light commonly for the second group of chips based on the reflectance of the at least one representative chip.

Preferably, according to an eighth aspect of the present invention, in the defect inspection apparatus of any one of the first to third aspects, the object is a chip having a plurality of regions into which different types of semiconductor devices are fabricated; the data generator generates the illumination light control data based on the reflectance of each of the regions; and the light intensity controller controls the intensity of the light for each of the regions.

Preferably, according to a ninth aspect of the present invention, in the defect inspection apparatus of any one of the first to third aspects, the object is a chip having a plurality of regions into which different types of semiconductor devices are fabricated; the inspector receives information concerning a fatal region in which the presence of the defect is fatal to the chip and information concerning a critical size of the defect which is fatal to the chip in the form of data; and the inspector detects only the defect occurring in the fatal region and having a size not less than the critical size, based on the data.

The defect inspection apparatus according to the first aspect of the present invention comprises the light intensity controller capable of correcting a difference in light reflectance in the surface to be inspected because of uneven film thicknesses, to suppress the generation of noises, thereby increasing the accuracy of defect detection.

In accordance with the second aspect of the present invention, the liquid crystal filter is higher in controllability and response speed, achieving minuter filter control.

In accordance with the third aspect of the present invention, proper control of the intensity of light directed from the light illuminator onto the surface to be inspected allows the properly uniform intensity of the light reflected from the surface.

In accordance with the fourth aspect of the present invention, the wafer having a surface coated with a film is inspected for defects, particularly extraneous material, with high accuracy.

In accordance with the fifth aspect of the present invention, light intensity control for each chip or for each die increases the accuracy of the defect inspection.

In accordance with the sixth aspect of the present invention, the determination of the reflectance of a reduced number of chips requires shorter time for inspection than the determination of the reflectance of chips or dice on a one-by-one basis.

In accordance with the seventh aspect of the present invention, the inspection of the second group of chips less susceptible to defects is advantageous in that the determination of the reflectance of a reduced number of chips requires shorter time for inspection than the determination of the reflectance of chips or dice on a one-by-one basis. Additionally, the inspection of the first group of chips more susceptible to defects is advantageous in that the determination of the reflectance for each chip or for each die increases the inspection accuracy.

In accordance with the eighth aspect of the present invention, light intensity control for each of the regions increases the accuracy of the defect inspection.

In accordance with the ninth aspect of the present invention, the inspector does not identify a defect occurring in other than the fatal region and a defect occurring in the fatal region and having a size less than the critical size as being defective. This allows the efficient detection of only fatal defects affecting a product yield.

It is therefore an object of the present invention to provide a defect inspection apparatus capable of detecting a defect in an object to be inspected with high accuracy and with efficiency.

These and other objects, features, aspects and advantages of the present invention will become more apparent from the following detailed description of the present invention when taken in conjunction with the accompanying drawings.

BRIEF DESCRIPTION OF THE DRAWINGS

FIG. 1 is a block diagram of a defect inspection apparatus according to a first preferred embodiment of the present invention;

FIG. 11 is a conceptual view showing a chip classification method;

FIGS. 12 through 14 are conceptual views showing other chip classification methods;

DESCRIPTION OF THE PREFERRED EMBODIMENTS

First Preferred Embodiment

Figure 2:
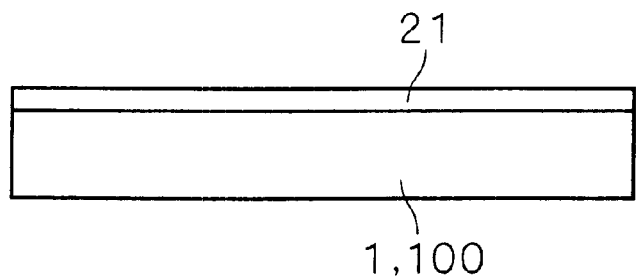
FIG. 2 is a side view of a wafer to be inspected or a sample wafer according to the first preferred embodiment of the present invention.

FIG. 1 is a block diagram of a defect inspection apparatus according to a first preferred embodiment of the present invention. A wafer 1 to be inspected or a sample wafer 100 is placed on an X-Y stage 2. The sample wafer 100 termed herein means a wafer similar in construction to the wafer 1 and having no defects. FIG. 2 is a side view of the wafer 1 or the sample wafer 100 according to the first preferred embodiment. A film 21 is formed on the entire surface of the wafer 1 and the sample wafer 100. Such a wafer with the film formed on the surface thereof is generally also referred to as a "film-coated wafer."

Referring again to FIG. 1, a detection optical system 6 such as a lens is disposed over the wafer 1 or the sample wafer 100, and a detector 7 such as TV camera or a photomultiplier is disposed over the detection optical system 6. An illumination light source 4 is disposed above the wafer 1 or the sample wafer 100 in angular relation thereto. A filter 5 for chronologically adjusting the intensity of light emitted from the illumination light source 4 is disposed between the illumination light source 4 and the wafer 1 or the sample wafer 100. The filter 5 may be a general attenuator type filter having a mechanism for rotating a polarizer. A reflected light intensity measurement section 11 having a light detector is disposed above the wafer 1 or the sample wafer 100 in angular relation thereto.

An output of the reflected light intensity measurement section 11 is connected to an input of a first main controller 12. An output of the first main controller 12 is connected to an input of a data storage section 13 and an input of an X-Y stage driver 3. An output of the data storage section 13 is connected to an input of a second main controller 9. An output of the X-Y stage driver 3 is connected to an input of the X-Y stage 2.

An output of the detector 7 is connected to an input of a detected data storage section 8. An output of the detected data storage section 8 is connected to an input of the second main controller 9. An output of the second main controller 9 is connected to an input of an external communication device 10, an input of the X-Y stage driver 3, and an input of a filter controller 14. An output of the filter controller 14 is connected to an input of the filter 5.

Description will be given on a method of inspecting the wafer 1 for defects, using the defect inspection apparatus shown in FIG. 1. First, data D1 concerning the shape of the sample wafer 100 (corresponding to data concerning the contour of the sample wafer 100 in the first preferred embodiment) is inputted from the exterior to the first main controller 12, and the sample wafer 100 is placed on the X-Y stage 2. The first main controller 12 produces coordinate data D2 based on the data D1 to input the coordinate data D2 to the X-Y stage driver 3. The X-Y stage driver 3 outputs a drive signal S1 based on the coordinate data D2. The X-Y stage 2 is driven in response to the drive signal S1 to move the sample wafer 100 to a predetermined position represented by the coordinate data D2. Then, illumination light L2 is directed from the illumination light source 4 onto the sample wafer 100. The illumination light L2 is reflected from the surface of the sample wafer 100, and the reflected light intensity measurement section 11 receives the reflected light L3.

The reflected light intensity measurement section 11 measures the intensity of the reflected light L3 to input data D3 concerning the intensity of the reflected light L3 to the first main controller 12. The first main controller 12 has externally previously inputted data D4 concerning the intensity of the illumination light L2. Based on the data D3 and D4, the first main controller 12 calculates the reflectance of the sample wafer 100 in the position represented by the coordinate data D2.

The first main controller 12 repeatedly updates and outputs the coordinate data D2 based on the data D1 to calculate the reflectance of the sample wafer 100 in a plurality of positions in the wafer surface by the above described operation. More specifically, as shown in FIGS. 3 and 4, the intensity of the reflected light L3 is measured at each point 22 while the illumination light L2 scans the surface of the sample wafer 100 at a constant pitch, and the reflectance at each point 22 is calculated based on the intensity of the reflected light 13.

Figure 3:
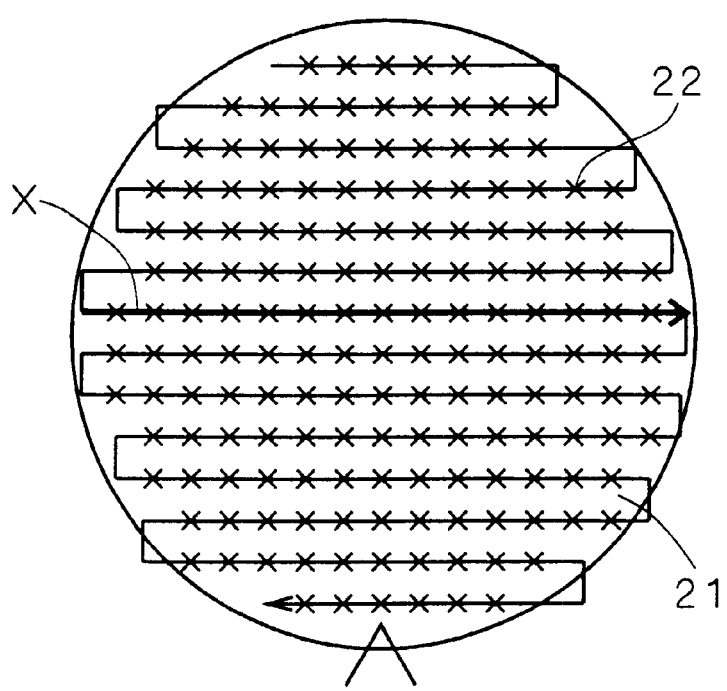
FIGS. 3 and 4 are views for schematically illustrating procedures of reflectance measurement in a plurality of positions in a wafer surface.
Figure 4:
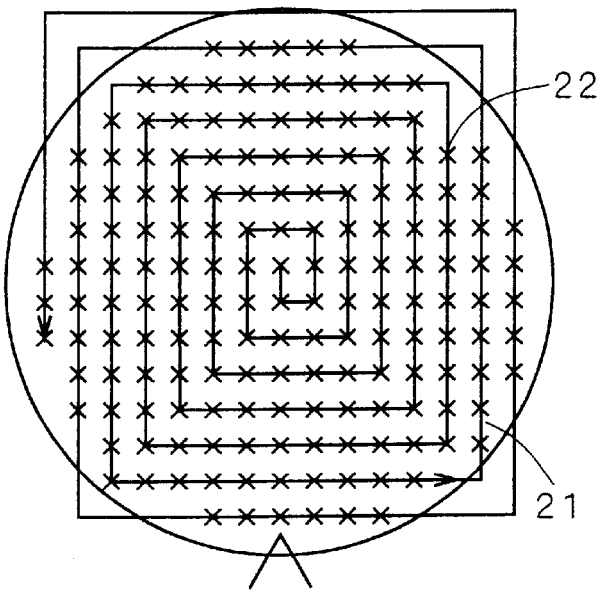
Figure 5:
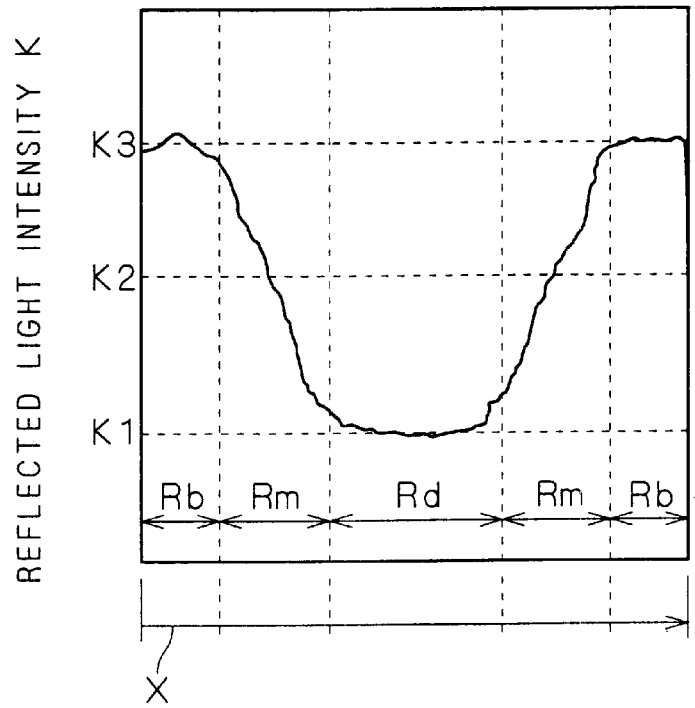
FIG. 5 shows a result of the intensity of reflected light L3 measured along the line X of FIG. 3.
Figure 6:
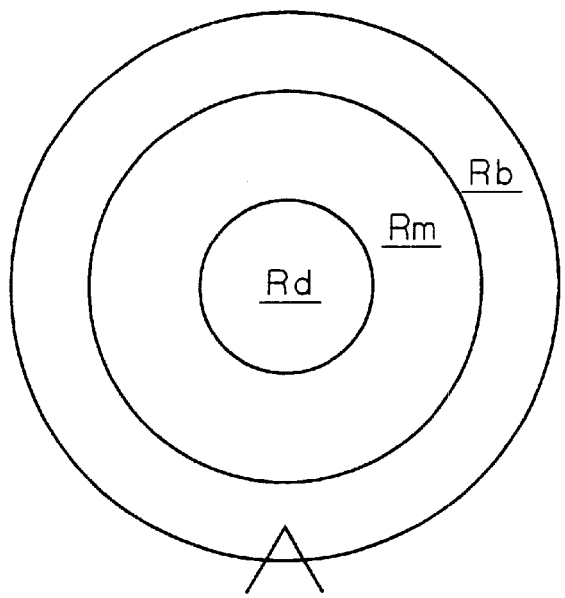
FIGS. 6 and 7 illustrate distributions of the intensity of the reflected light L3 in the wafer surface.
Figure 7:
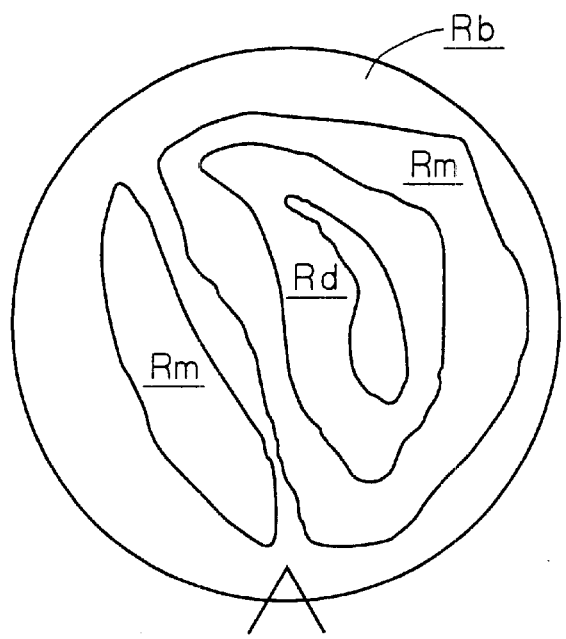

FIG. 5 shows a result of the intensity of the reflected light L3 measured along the line X of FIG. 3. Based on the reflected light intensity K, the wafer surface is divided into three regions: a region Rd in which K approximately equals K1; a region Rm in which K1<K<K3; and a region Rb in which K approximately equals K3. FIGS. 6 and 7 illustrate distributions of the intensity of the reflected light L3 in the wafer surface. The intensity of the reflected light L3 exhibits a concentric distribution in FIG. 6, and a local distribution in FIG. 7. In particular, wafers subjected to the CMP process often exhibit the distribution shown in FIG. 6.

Referring again to FIG. 1, the first main controller 12 calculates an average intensity value K2 of the reflected light L3 based on the resultant intensity distribution of the reflected light L3 to input reference data D5 concerning the average intensity value K2 to the data storage section 13. Further, the first main controller 12 produces a reflectance distribution in the wafer surface, and produces illumination light control data D6 based on the reflectance distribution to input the illumination light control data D6 to the data storage section 13. The illumination light control data D6 is control data for adjusting the intensity of the illumination light L2 so that the intensity of the reflected light L3 reaches the average intensity value K2 in all locations in the wafer surface. The data storage section L3 stores therein the reference data D5 and the illumination light control data D6 inputted thereto.

Next, the data D1 concerning the shape of the wafer 1 is inputted from the exterior to the second main controller 9, and the wafer 1 is placed on the X-Y stage 2. The second main controller 9 produces the coordinate data D2 to input the coordinate data D2 to the X-Y stage driver 3. The X-Y stage driver 3 outputs the drive signal S1 based on the coordinate data D2. The X-Y stage 2 is driven in response to the drive signal S1 to move the wafer 1 to a predetermined position represented by the coordinate data D2.

The second main controller 9 receives the illumination light control data D6 from the data storage section L3 to input the illumination light control data D6 to the filter controller 14. During this operation, illumination light L1 is emitted from the illumination light source 4 to the filter 5.

The filter controller 14 produces a filter control signal S2 based on the inputted illumination light control data D6 to input the filter control signal S2 to the filter 5. The filter control signal S2 controls the transmittance or reflectance of the filter 5 for the illumination light L1. As a result, the illumination light L2 with the intensity controlled by the filter 5 is directed to the position of the wafer 1 which is represented by the coordinate data D2. The illumination light L2 is reflected from (or scattered by) the surface of the wafer 1. The reflected light (or the scattered light) L4 is collected by the detection optical system 6 and then detected by the detector 7. A detected signal from the detector 7 in the form of detected data D7 is inputted to and stored in the detected data storage section 8.

Figure 8:
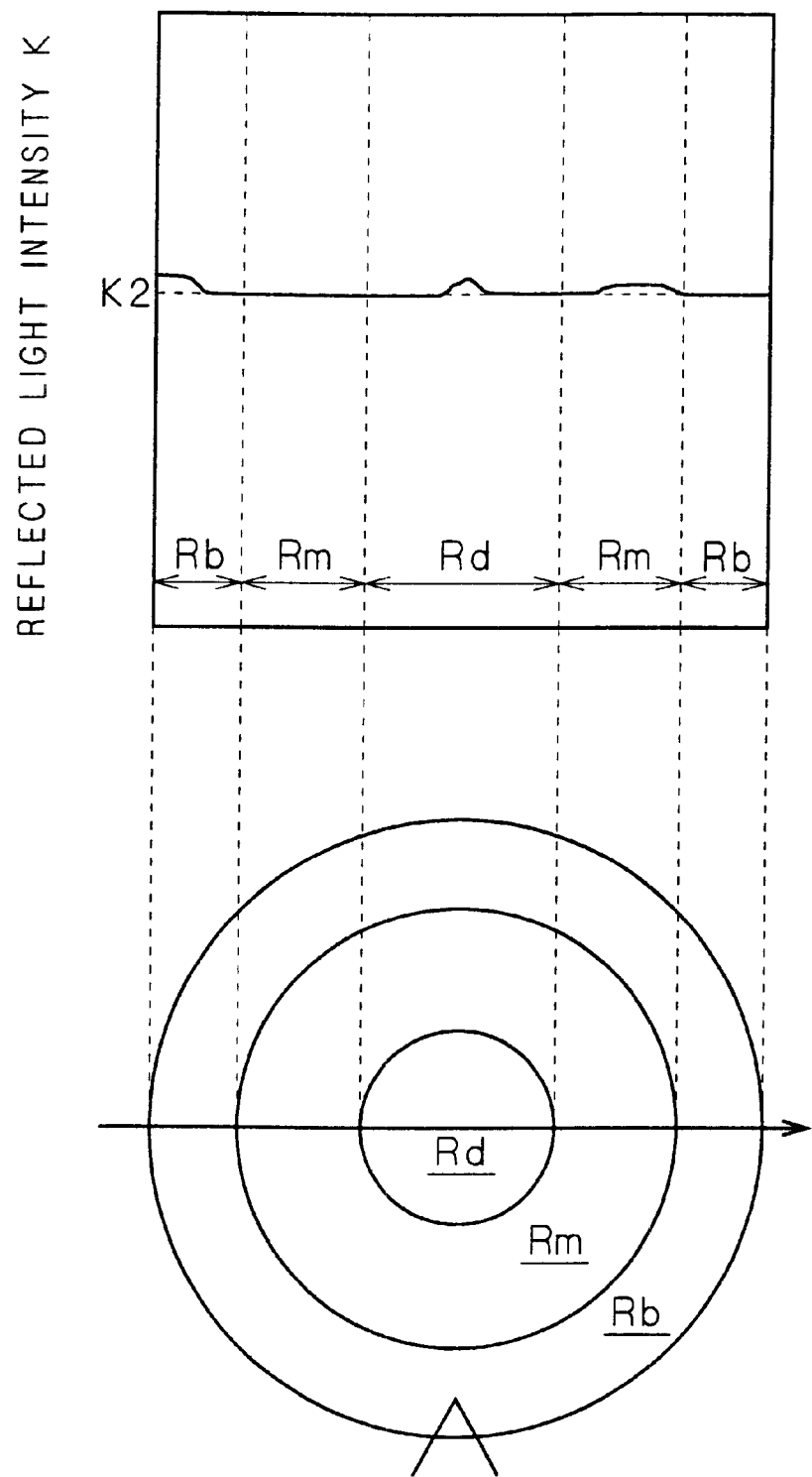
FIG. 8 shows a distribution of the intensity of reflected light L4 after filter control.

The second main controller 9 repeatedly updates and outputs the coordinate data D2, based on the data D1. The above described operation is repeatedly performed on the positions in the surface of the wafer 1 while the transmittance or reflectance of the filter 5 for the illumination light L1 is chronologically controlled in accordance with the positions in the surface of the wafer 1 which are represented by the coordinate data D2. FIG. 8 shows a distribution of the intensity of the reflected light L4 after the control of the filter 5. It will be found from FIG. 8 that the intensity K of the reflected light L4 is controlled approximately at the average intensity value K2 in all positions in the regions Rb, Rm and Rd.

Figure 9:
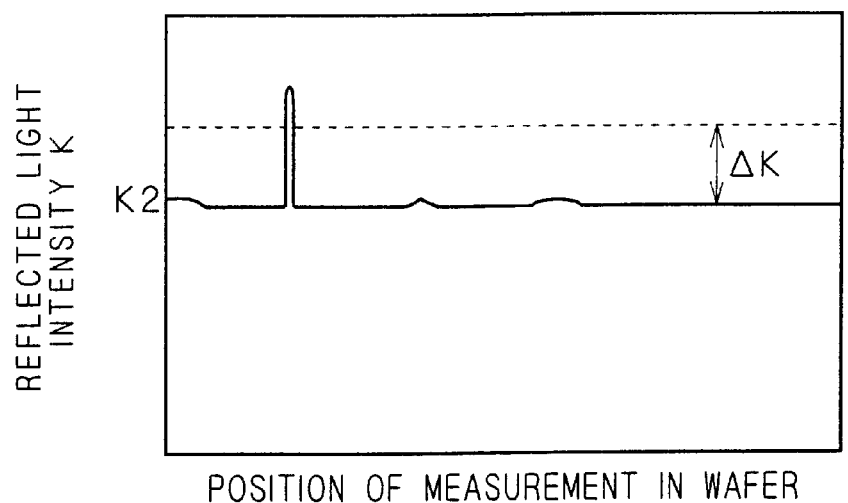
FIG. 9 illustrates a defect judgement method in a second main controller.

The second main controller 9 receives a detected data row D8 from the detected data storage section 8, and receives the reference data D5 from the data storage section 13. Then, the second main controller 9 makes a comparison between the detected data row D8 and the reference data D5. The second main controller 9 judges that a defect is present in the associated position in the wafer 1 if the intensity of the reflected light L4 represented by the detected data row D8 is deviated from the average intensity value K2 represented by the reference data D5 by a predetermined threshold value $\Delta K$ or greater as shown in FIG. 9 or the degree of deviation remarkably exceeds a statistical distribution value (e.g., a median value $\pm 3\sigma$ where $\sigma$ is a standard deviation).

A defect judgement result from the second main controller 9 is inputted in the form of data D9 to the external communication device 10, and the external communication device 10 outputs the defect judgement result in the form of data D10 to the exterior of the apparatus.

In the above description, the illumination light source 4 used for inspection of the wafer 1 for defects is used to determine the reflectance distribution. However, the same illumination light source need not always be used. Different illumination light sources may be used if the same effects are produced.

Further, in the above description, the reflectance distribution is determined using the sample wafer 100 before the initiation of the inspection of the wafer 1 for defects. Instead, the wafer 1 itself may be used, rather than the sample wafer 100, to determine the reflectance distribution during the inspection of the wafer 1 for defects or during the production of an inspection recipe. If wafers 1 to be inspected differ from each other in film thickness distribution, the reflectance distribution must be determined for each of the wafers 1.

Furthermore, in the above description, the second main controller 9 judges that there is a defect if the intensity of the reflected light L4 is greatly deviated from the average intensity value K2 or the degree of deviation remarkably exceeds the statistical distribution value. However, it is sufficiently practicable to use the algorithm of detecting defects based on the difference image which has been used in the background art defect inspection apparatus.

In the defect inspection apparatus according to the first preferred embodiment, as described hereinabove, the light reflectance distribution in the wafer surface is previously determined, and the filter 5 controls the intensity of the illumination light L2 so that the intensity of the reflected light L4 from the wafer 1 is uniform in the wafer surface during the inspection. Therefore, the defect inspection apparatus according to the first preferred embodiment can suppress the generation of noises to increase the accuracy of defect detection even if the difference in film thickness causes the difference in reflected light intensity in the wafer surface.

Second Preferred Embodiment

Figure 10:
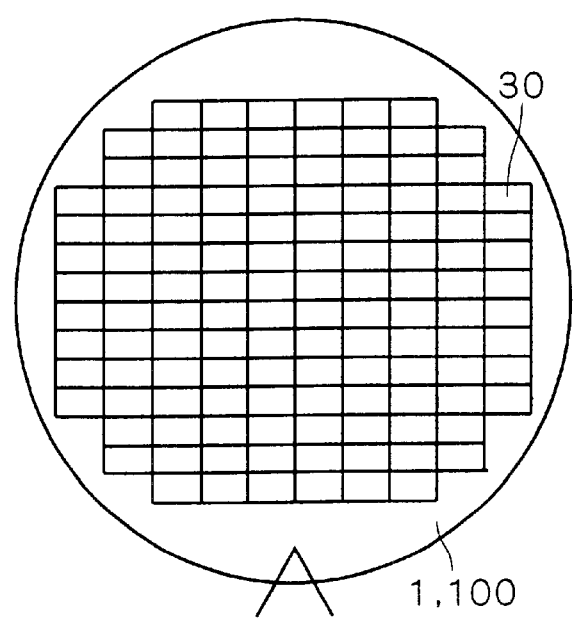
FIG. 10 is a top plan view showing a chip arrangement pattern in the wafer.

A second preferred embodiment according to the present invention proposes a method of applying the defect inspection apparatus of the first preferred embodiment to the inspection of a patterned wafer, rather than the film-coated wafer, for defects. The "patterned wafer" termed herein means a wafer including a plurality of chips 30 arranged in a matrix to form a pattern, as shown in FIG. 10.

Description will be given on a method of inspecting the wafer 1 for defects, using the defect inspection apparatus shown in FIG. 1, mainly about the difference from the first preferred embodiment. First, the data D1 concerning the shape of the sample wafer 100 (corresponding to data concerning the arrangement pattern of the chips 30 in the surface of the sample wafer 100 according to the second preferred embodiment) is inputted from the exterior to the first main controller 12. The reflected light intensity measurement section 11 measures the intensity of the reflected light L3 in a plurality of locations (preferably three locations or more) in any chip 30 (referred to as an "objective chip" for purposes of convenience). The plurality of locations of measurement may be taught to the apparatus by an operator or selected by the apparatus in a random fashion based on the data D1. The first main controller 12 calculates the average value of the measured intensities to recognize the average value as the intensity of the reflected light L3 from the objective chip 30. The first main controller 12 calculates the reflectance of the objective chip 30 based on the intensity of the reflected light L3 from the objective chip 30. In the above description, the first main controller 12 recognizes the average value of the intensities of the reflected light L3 from the respective locations in a chip 30 as the intensity of the reflected light L3 from that chip 30. Alternatively, the intensity of the reflected light L3 from one location in the chip 30 may be measured as a representative and recognized as the intensity of the reflected light L3 from the chip 30.

The above-mentioned operation is repeatedly performed on all of the chips 30 in the sample wafer 100 to determine the intensities of the reflected light L3 from the respective chips 30, the average intensity value K2 thereof, and the reflectances of the respective chips 30. The first main controller 12 produces the illumination light control data D6 for adjusting the intensity of the illumination light L2 so that the intensity of the reflected light L3 from all of the chips 30 reaches the average intensity value K2.

For the execution of the inspection of the wafer 1 for defects, the filter controller 14 individually changes the reflectance or transmittance of the filter 5 for each chip 30, based on the illumination light control data D6.

In the defect inspection apparatus according to the second preferred embodiment, as described hereinabove, the reflectance of each chip 30 is previously determined, and the filter 5 controls the intensity of the illumination light L2 so that the intensities of the reflected light L4 from the respective chips 30 are uniform during the inspection. Therefore, the defect inspection apparatus according to the second preferred embodiment can suppress the generation of noises to increase the accuracy of defect detection even if the difference in film thickness causes the difference in reflected light intensity between the chips 30.

In the above description, the reflectance is individually determined for each chip 30, and the intensity of the illumination light L2 is individually controlled for each chip 30. However, a set of chips of the same construction (which are referred to as a "die") are generally transferred or patterned as a unit in the process of manufacturing semiconductor devices. Thus, the reflectance may be determined for each die, and the intensity of the illumination light L2 may be controlled for each die. This reduces the time required to produce the illumination light control data D6.

Third Preferred Embodiment

The defect inspection apparatus according to the second preferred embodiment is required to individually determine the reflectance for each chip 30 or for each die because of the need to individually control the intensity of the illumination light L2 for each chip 30 or for each die. This is advantageous in making the intensity of the reflected light L4 uniform during the inspection to reduce noises, but tends to increase the time required for the inspection. A third preferred embodiment according to the present invention proposes the defect inspection apparatus based on the apparatus of the second preferred embodiment and capable of reducing the time required to inspect the patterned wafer for defects.

Description will be given on a method of inspecting the wafer 1 for defects, using the defect inspection apparatus shown in FIG. 1, mainly about the difference from the second preferred embodiment. First, the plurality of chips 30 arranged in the sample wafer 100 are classified into a plurality of groups. A film thickness distribution or a reflectance distribution after certain types of manufacturing processes is predictable to some extent. The film thickness distribution or the reflectance distribution is also predictable to some extent by referencing design data. Thus, the plurality of chips 30 are classified into the plurality of groups based on the predicted distribution. FIG. 11 shows an example of the classification. The plurality of chips 30 shown in FIG. 11 are classified into three groups R1 to R3 based on the predicted film thickness distribution after the CMP process. FIG. 12 shows another example of the classification. The classification shown in FIG. 12 is employed when the film thickness distribution and the reflectance distribution are not known but time does not permit the measurement of the reflectance for all chips or all dice.

Next, the data D1 concerning the shape of the sample wafer 100 (corresponding to data concerning the arrangement pattern of the chips 30 in the surface of the sample wafer 100 and the classification of the chips 30 according to the third preferred embodiment) is inputted from the exterior to the first main controller 12. The reflected light intensity measurement section 11 measures the intensity of the reflected light L3 from a plurality of typically specified chips 30 (preferably three chips or more) selected among the chips 30 included in the group R1. The plurality of typically specified chips 30 for measurement may be taught to the apparatus by an operator or selected by the apparatus in a random fashion based on the data D1. The first main controller 12 calculates the average value of the measured intensities to recognize the average value as the intensity of the reflected light L3 from all of the chips 30 included in the group R1. The first main controller 12 calculates the reflectance based on the intensity of the reflected light 13. In the above description, the first main controller 12 recognizes the average value of the intensities of the reflected light L3 from the respective specified chips 30 as the intensity of the reflected light L3 from all chips 30 included in the group R1. Alternatively, the intensity of the reflected light L3 from one of the chips 30 included in the group R1 may be measured as a representative and recognized as the intensity of the reflected light L3 from all chips 30 included in the group R1.

The above-mentioned operation is repeatedly performed on the groups R2 and R3 to determine the intensities of the reflected light L3 from the respective groups of the chips 30 and the reflectances of the respective groups of the chips 30 and to calculate the average intensity value K2 of the reflected light L3 from the chips 30. The first main controller 12 produces the illumination light control data D6 for adjusting the intensity of the illumination light L2 so that the intensity of the reflected light L3 from all of the groups R1 to R3 reaches the average intensity value K2.

For the execution of the inspection of the wafer 1 for defects, the filter controller 14 individually changes the reflectance or transmittance of the filter 5 for each of the groups R1 to R3, based on the illumination light control data D6.

In the defect inspection apparatus according to the third preferred embodiment, as described hereinabove, the reflectance of the chips 30 is individually determined for each of the groups R1 to R3, and the filter 5 controls the intensity of the illumination light L2 for each of the groups R1 to R3 during the inspection. Therefore, the defect inspection apparatus according to the third preferred embodiment determines the reflectance of a smaller number of chips 30 to require shorter time for inspection than the apparatus of the second preferred embodiment in which the reflectance is individually determined for each chip or for each die.

Figure 13:
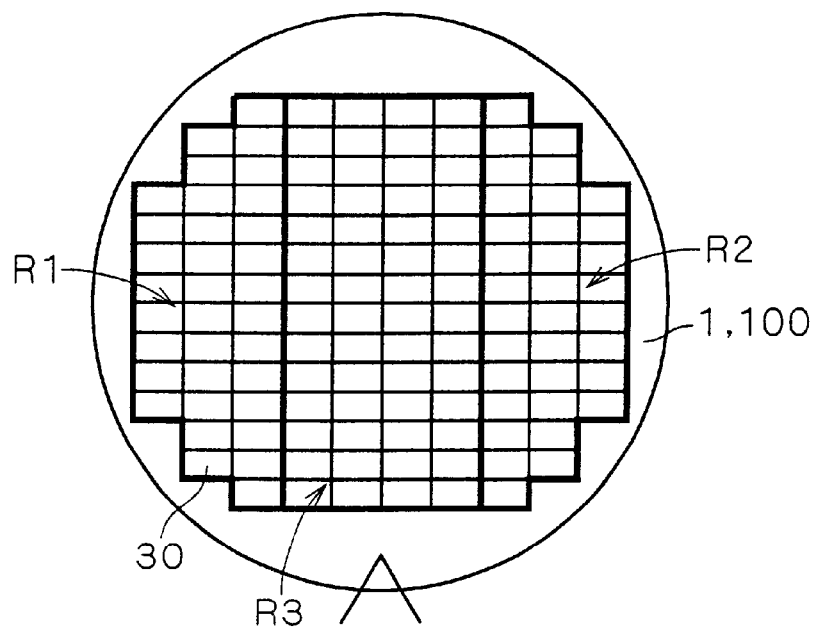
Figure 14:
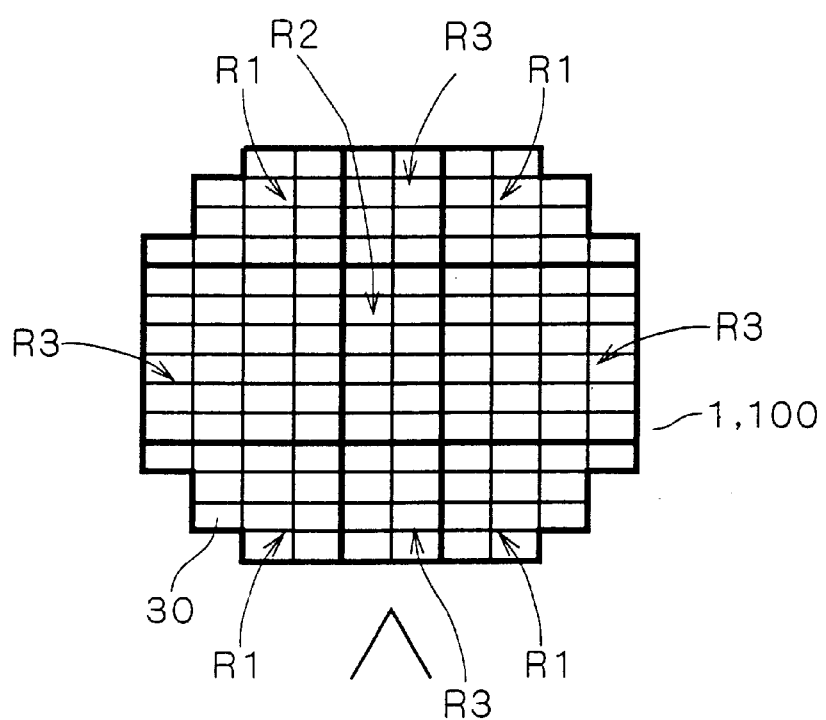

FIGS. 13 and 14 show other examples of the classification. The plurality of chips 30 of FIGS. 13 and 14 are classified into the three groups R1 to R3 in accordance with susceptibility to defects when a region susceptible to defects in the wafer is empirically known. Specifically, it is assumed that the chips 30 included in the groups R1 and R2 are more susceptible to defects, and the chips 30 included in the group R3 are less susceptible to defects. In particular, the distribution shown in FIG. 14 is effective for the defect inspection which follows the process of forming a deposition film using low-pressure CVD equipment such as a diffusion furnace.

The chips 30 included in the group R3 less susceptible to defects are inspected in a manner described below. The reflectance of at least one typically specified chip 30 selected among the chips 30 included in the group R3 is determined as above described. During the inspection, the intensity of the illumination light L2 is controlled commonly for the chips 30 included in the group R3, based on the typically determined reflectance. On the other hand, the chips 30 included in the groups R1 and R2 more susceptible to defects are inspected in a manner described in the second preferred embodiment. Specifically, the reflectance of each chip 30 or each die is individually determined, and the intensity of the illumination light L2 is individually controlled for each chip 30 or for each die during the inspection. This reduces the time required for inspection in the region less susceptible to defects, and improves the accuracy of inspection in the region more susceptible to defects.

Fourth Preferred Embodiment

Figure 15:
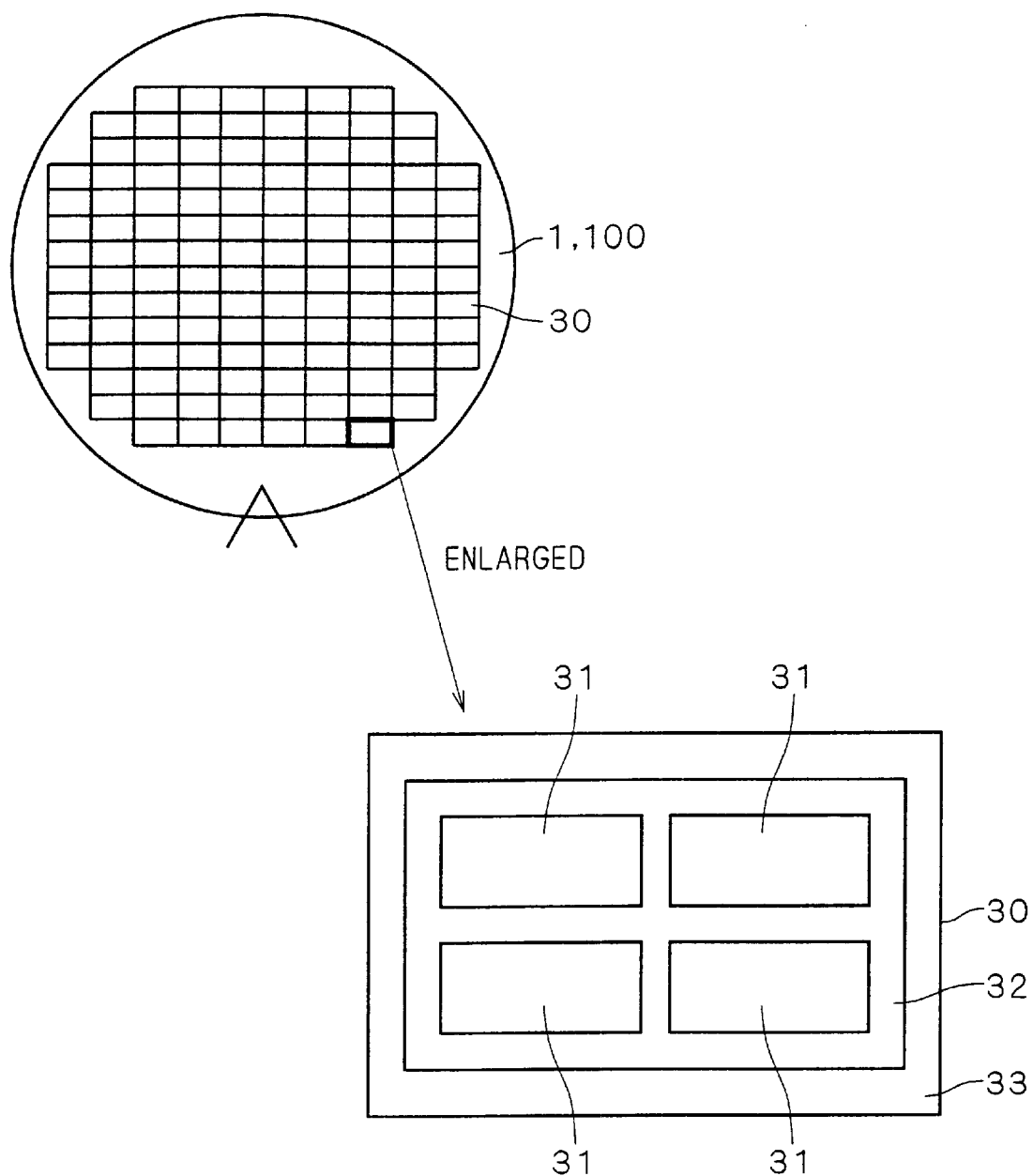
FIG. 15 is a schematic top plan view of a chip configuration.

FIG. 15 is a schematic top plan view of a configuration of the chips 30. A single chip 30 has a plurality of regions 31 to 33 into which different types of semiconductor devices are fabricated. The regions 31 to 33 differ from each other in pattern fineness or in the presence or absence of patterns. For example, a chip for a memory circuit such as a DRAM has a quite minute pattern region known as a memory cell region and a peripheral circuit region for controlling memory cells. In recent years, a number of hybrid circuits each including a logic circuit and a memory circuit both fabricated into a single chip have been found. There arises a difference in reflectance between regions of a illuminated chip because of the difference in pattern fineness or the presence or absence of patterns or because of uneven film thicknesses resulting from the difference in pattern fineness or the presence or absence of patterns. A fourth preferred embodiment according to the present invention proposes the defect inspection apparatus for inspecting a chip having a plurality of regions differing in reflectance.

A laser light source is used as the illumination light source 4 of the defect inspection apparatus of FIG. 1 in the fourth preferred embodiment. This allows the use of a beam of illumination light L2 which is very small in diameter for the defect inspection. In this case, it is desirable that the detector 7 and the light detector of the reflected light intensity measurement section 11 employ a detector designed specifically for laser light.

Although not shown in FIG. 1, the defect inspection apparatus may comprise an optical system of a bright field microscope type. In this case, a minimum resolvable region is determined by the size of the detected image. This image size is sufficiently small to allow the detection optical system itself to be used to measure the intensity of the reflected light L4.

Description will be given on a method of inspecting a chip 30 for defects. First, the data D1 concerning the shape of a nondefective chip (referred to hereinafter as a "sample chip") 30 (corresponding to data concerning the arrangement pattern of the regions 31 to 33 in a surface to be inspected of the sample chip 30 according to the fourth preferred embodiment) is inputted from the exterior to the first main controller 12. The sample chip 30 selected herein may be any chip 30 in the sample wafer 100.

Figure 16:
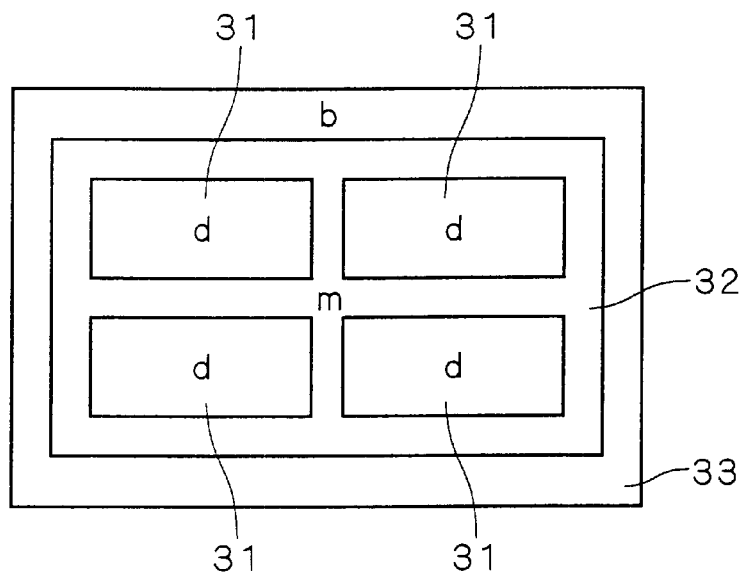
FIG. 16 is a schematic view of a result of the intensity of the reflected light 13 measured from individual sample chip regions.
Figure 17:
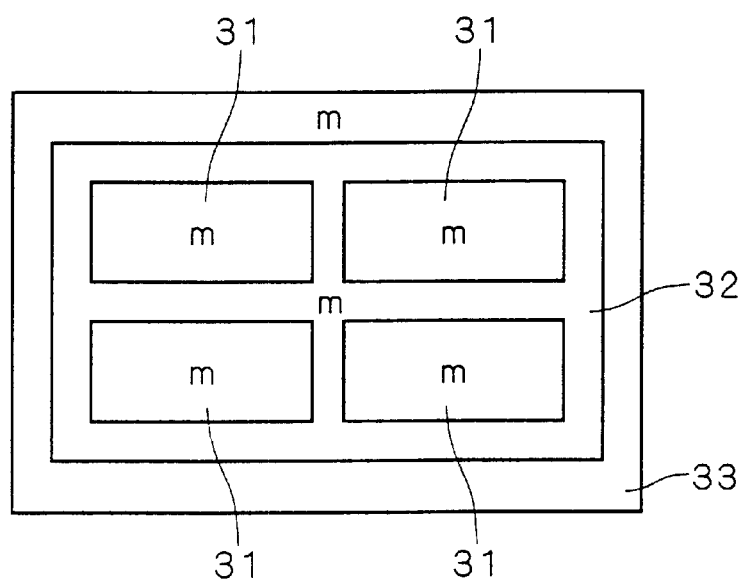
FIG. 17 is a schematic view of a distribution of the intensity of the reflected light L4 from the regions after the filter control.

The reflected light intensity measurement section 11 measures the intensity of the reflected light L3 for each of the regions 31 to 33 of the sample chip 30 in the above described manner. FIG. 16 is a schematic view of an intensity measurement result which shows that the intensity of the reflected light L3 is high (as designated by the reference character b) in the region 33, low (as designated by the reference character d) in the region 31, and has an intermediate value therebetween (as designated by the reference character m) in the region 32. The filter controller 14 uses the filter 5 to control the intensity of the illumination light L2 so that the intensities of the reflected light L4 from the respective regions 31 to 33 are uniform throughout the surface of a chip 30 being inspected in the above described manner. FIG. 17 is a schematic view of the intensity distribution of the reflected light L4 from the regions 31 to 33 after the control of the filter 5. It will be found from FIG. 17 that the intensities of the reflected light L4 from the respective regions 31 to 33 have the intermediate value (as designated by the reference character m) and are corrected to provide uniformity.

In the defect inspection apparatus according to the fourth preferred embodiment, as described hereinabove, the reflectance of each of the regions 31 to 33 of the chip 30 is previously determined, and the filter 5 controls the intensity of the illumination light L2 so that the intensities of the reflected light L4 from the respective regions 31 to 33 are uniform during the inspection. Therefore, the defect inspection apparatus according to the fourth preferred embodiment can suppress the generation of noises to increase the accuracy of defect detection even if the difference in pattern fineness or the presence or absence of patterns causes the difference in reflected light intensity between the regions 31 to 33 of the chip 30.

The process of rendering uniform the reflected light intensity in the wafer surface as described in the above preferred embodiments may be performed in addition to the process of rendering uniform the reflected light intensity in the chip. If only the process of rendering uniform the reflected light intensity in the wafer surface is performed but the process of rendering uniform the reflected light intensity in the chip is not performed, a sufficient increase in wafer-level inspection accuracy is accomplished.

Fifth Preferred Embodiment

Figure 18:
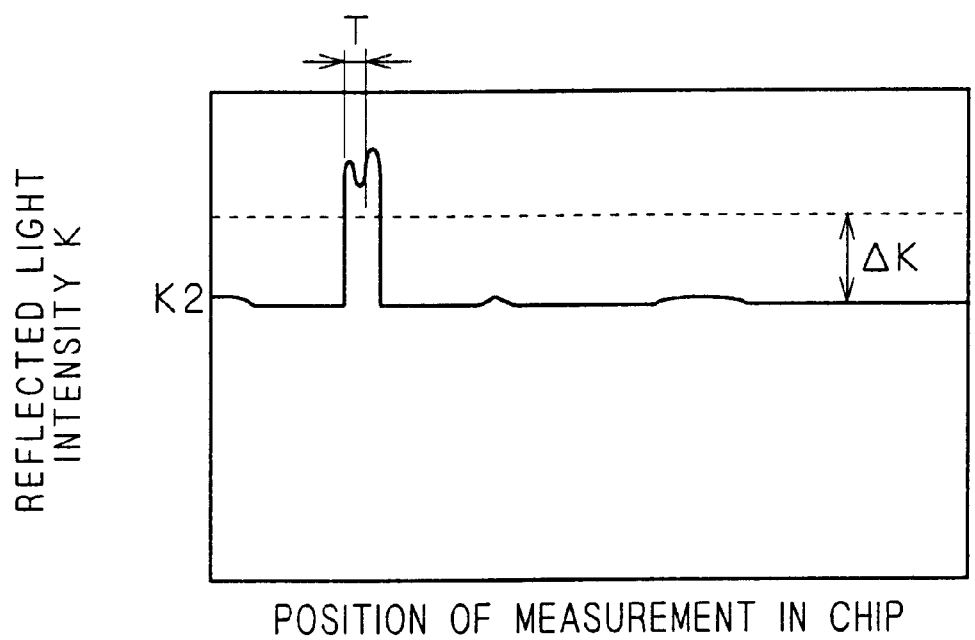
FIG. 18 illustrates a defect judgement method in the second main controller.
Figure 19:
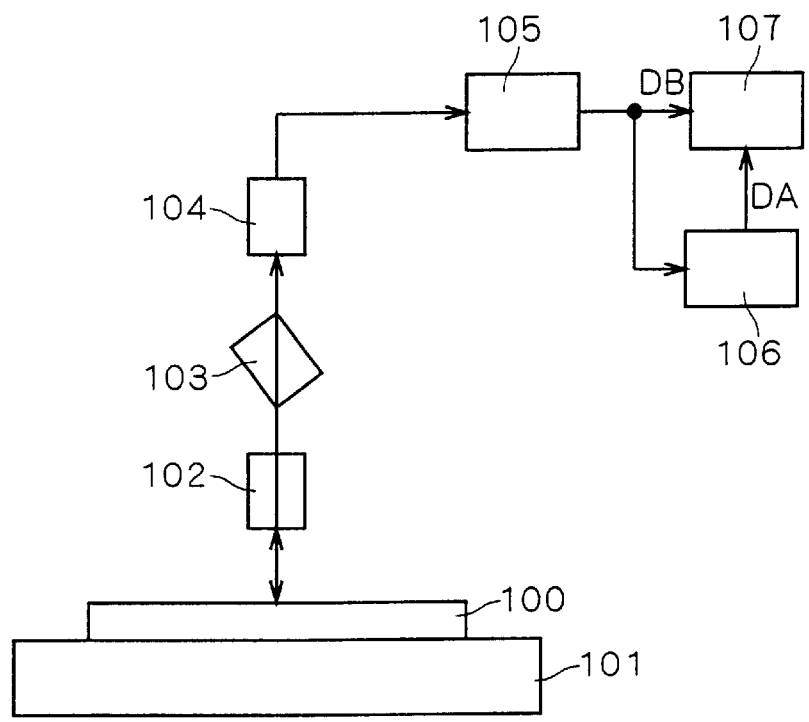
FIG. 19 is a schematic block diagram of a background art defect inspection apparatus.
Figure 20:
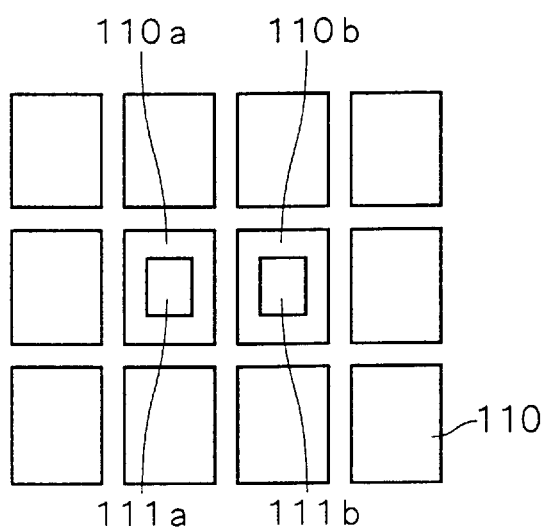
FIG. 20 is a partially enlarged top plan view of a wafer configuration.
Figure 21:
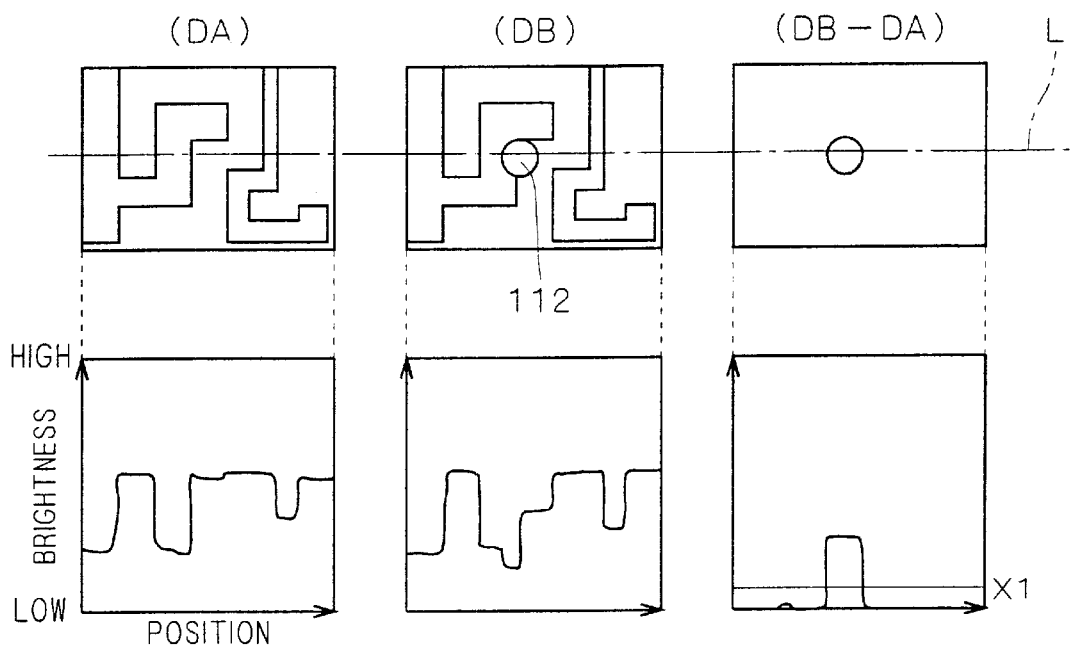
FIG. 21 shows image data DA, DB and difference data DB−DA.
Figure 22:
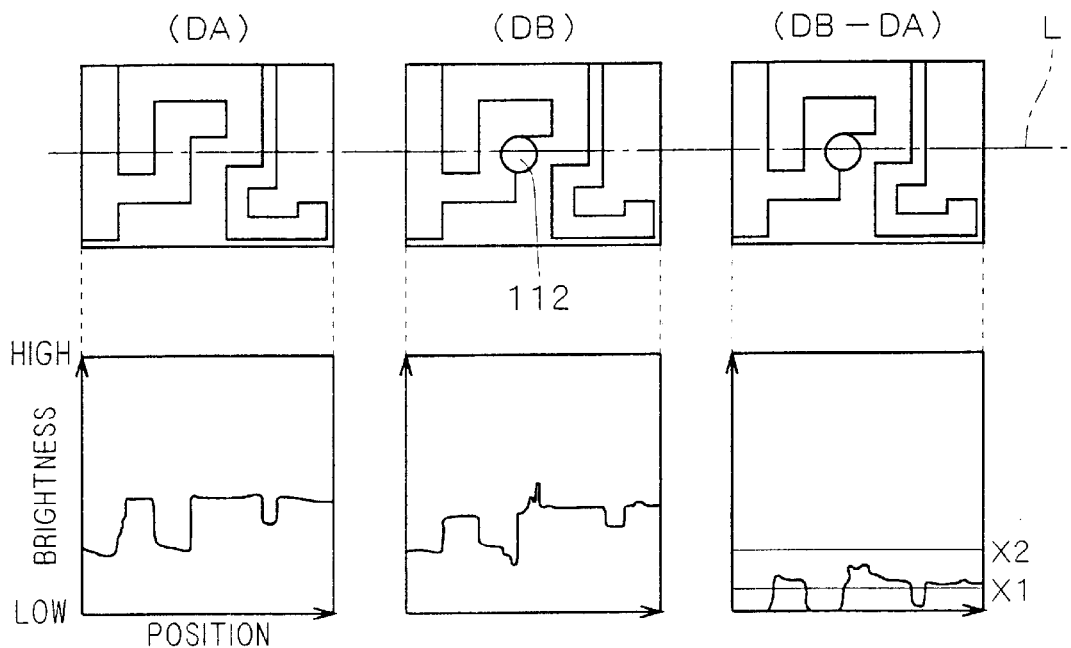
FIG. 22 illustrates problems with the background art defect inspection apparatus.

According to a fifth preferred embodiment of the present invention, a critical size of defects is individually set for each of the regions 31 to 33 of the chip 30 and previously inputted in the form of data to the second main controller 9 in the defect inspection apparatus of the fourth preferred embodiment. The critical size is determined based on device design standards and has different values depending on the types of processes and films. For example, the critical size may be set at one-half to one-third of a wiring pitch. During the inspection, the second main controller 9 identifies a detected defect having a size not less than the critical size T as being defective, as shown in FIG. 18.

The defect inspection apparatus according to the fifth preferred embodiment, in which the second main controller 9 does not identify a detected defect having a size less than the critical size T as being defective, can efficiently detect only a fatal defect which affects a product yield.

Additionally, information about the position of a fatal region in the chip 30 may be previously inputted in the form of data to the second main controller 9. The fatal region termed herein means a region in which the presence of a defect is fatal to a device. For instance, a densely patterned region may be set as the fatal region. This allows the second main controller 9 to identify only a fatal defect occurring in the fatal region as being defective.

Sixth Preferred Embodiment

Although the attenuator type filter is used as the filter 5 in the first preferred embodiment, a liquid crystal filter capable of controlling light transmittance depending on applied voltage may be used as the filter 5. Examples of the liquid crystal filter used herein include a liquid crystal filter of a liquid crystal shutter type which uniformly changes light transmittance in a filter surface, and a liquid crystal filter of a liquid crystal projection type which has a matrix electrode and is capable of non-uniformly controlling light transmittance in the filter surface in response to an image information input.

As described hereinabove, the defect inspection apparatus according to the sixth preferred embodiment of the present invention comprises the liquid crystal filter serving as the filter 5. The liquid crystal filter is higher in controllability and in reaction speed than the attenuator type filter, achieving minuter filter control.

The use of the liquid crystal filter of the liquid crystal projection type provides an in-surface distribution of light transmittance in the filter surface, and also allows the in-surface distribution to change depending on an illuminated region. Therefore, the intensity of the illumination light L2 is properly controlled, and the intensity of the reflected light L4 is rendered properly uniform in the surface being inspected.

While the invention has been described in detail, the foregoing description is in all aspects illustrative and not restrictive. It is understood that numerous other modifications and variations can be devised without departing from the scope of the invention.

What is claimed is:

1. A defect inspection apparatus comprising:
   a light illuminator configured to direct light onto a surface of an object to be inspected;
   a data generator configured to generate illumination light control data for rendering the intensity of light reflected from said surface uniform throughout said surface, based on a result obtained by detecting a distribution of reflectance of said surface for said light;
   a light intensity controller configured to control the intensity of said light directed from said light illuminator onto said surface, based on said illumination light control data; and
   an inspector configured to receive said light reflected from said surface or scattered by said surface and to inspect said surface for a defect.

2. The defect inspection apparatus according to claim 1, wherein said light intensity controller includes:
   a liquid crystal filter having a filter surface disposed in an optical path between said light illuminator and surface; and
   a filter controller configured to control transmittance of said filter surface for said light, based on said illumination light control data.

3. The defect inspection apparatus according to claim 2, wherein said liquid crystal filter is a filter configured to non-uniformly control said transmittance in said filter surface.

4. The defect inspection apparatus according to claim 1, wherein said object is a wafer having a surface coated with a film.

5. The defect inspection apparatus according to claim 4, wherein said data generator measures the intensity of said light reflected at a plurality of points while scanning a wafer surface of said wafer at a constant pitch to obtain said distribution of the reflectance of said wafer surface for said light.

6. The defect inspection apparatus according to claim 1, wherein said object is a wafer having a plurality of chips arranged in a matrix;
   wherein said data generator generates said illumination light control data based on said reflectance for each of said chips or for each of dice; and
   wherein said light intensity controller controls the intensity of said light for each of said chips or for each of said dice.

7. The defect inspection apparatus according to claim 1, wherein said object is a wafer having a plurality of chips arranged in a matrix;
   wherein said data generator receives classification data concerning said plurality of chips classified into a first group of chips and a second group of chips in accordance with a predicted distribution of said reflectance of a wafer surface of said wafer;
   wherein said data generator determines a first reflectance of at least one representative first chip included in said first group as said reflectance of said first group of chips, and determines a second reflectance of at least one representative second chip included in said second group as said reflectance of said second group of chips; and
   wherein said light intensity controller controls the intensity of said light for each of said first and second groups.

8. The defect inspection apparatus according to claim 7, wherein said at least one representative first chip includes at least three first chips, and said at least one representative second chip includes at least three second chips; and
   wherein said data generator calculates an average value of said reflectances of said at least three first chips to determine said first reflectance, and calculates an average value of said reflectances of said at least three second chips to determine said second reflectance.

9. The defect inspection apparatus according to claim 1, wherein said object is a wafer having a plurality of chips arranged in a matrix;
   wherein said data generator receives classification data concerning said plurality of chips classified into a first group of chips expected to be more susceptible to defects and a second group of chips expected to be less susceptible to defects;
   wherein said data generator determines said reflectance for each of said first group of chips or for each of said dice of said first group of chips, and determines said reflectance of at least one representative chip included in said second group as said reflectance of said second group of chips; and
   wherein said light intensity controller controls the intensity of said light for each of said first group of chips or for each of said dice of said first group of chips, and controls the intensity of said light commonly for said second group of chips based on said reflectance of said at least one representative chip.

10. The defect inspection apparatus according to claim 1, wherein said object is a chip having a plurality of regions into which different types of semiconductor devices are fabricated;
    wherein said data generator generates said illumination light control data based on said reflectance of each of said regions; and
    wherein said light intensity controller controls the intensity of said light for each of said regions.

11. The defect inspection apparatus according to claim 1, wherein said object is a chip having a plurality of regions into which different types of semiconductor devices are fabricated;
    wherein said inspector receives information concerning a fatal region in which the presence of said defect is fatal to said chip and information concerning a critical size of said defect which is fatal to said chip in the form of data; and
    wherein said inspector detects only said defect occurring in said fatal region and having a size not less than said critical size, based on said data.

* * * * *